(12) United States Patent
Delacretaz

(10) Patent No.: US 8,657,537 B2
(45) Date of Patent: Feb. 25, 2014

(54) CUTTING INSTRUMENT AND METHODS FOR IMPLEMENTING SAME

(75) Inventor: Francis Delacretaz, Ballaigues (CH)

(73) Assignee: Maillefer Instruments Holding Sarl, Ballaigues (CH)

( * ) Notice: Subject to any disclaimer, the term of this patent is extended or adjusted under 35 U.S.C. 154(b) by 985 days.

(21) Appl. No.: 12/678,201

(22) PCT Filed: Nov. 13, 2007

(86) PCT No.: PCT/IB2007/003469
§ 371 (c)(1),
(2), (4) Date: Mar. 15, 2010

(87) PCT Pub. No.: WO2009/063261
PCT Pub. Date: May 22, 2009

(65) Prior Publication Data
US 2010/0209200 A1 Aug. 19, 2010

(51) Int. Cl.
*B23D 77/12* (2006.01)
*B23D 77/00* (2006.01)

(52) U.S. Cl.
USPC .................................... 407/54; 407/61

(58) Field of Classification Search
USPC .................. 407/54, 57, 61; 408/229, 211
See application file for complete search history.

(56) References Cited

U.S. PATENT DOCUMENTS

| | | | |
|---|---|---|---|
| 4,116,578 A * | 9/1978 | Gelfand et al. | 408/222 |
| 4,560,309 A * | 12/1985 | Hornsby | 408/229 |
| 4,634,378 A | 1/1987 | Leonard | |
| 5,000,630 A * | 3/1991 | Riley et al. | 408/228 |
| 5,236,291 A | 8/1993 | Agapiou et al. | |
| 5,478,179 A * | 12/1995 | Kress et al. | 408/199 |
| 5,855,458 A * | 1/1999 | Reynolds et al. | 407/54 |
| 5,975,899 A | 11/1999 | Badoz et al. | |
| 6,368,030 B1 * | 4/2002 | Sato et al. | 407/53 |
| 6,431,962 B1 | 8/2002 | George | |
| 6,547,495 B2 * | 4/2003 | Meece et al. | 408/1 R |

FOREIGN PATENT DOCUMENTS

| | | |
|---|---|---|
| DE | 44 05 749 | 8/1995 |
| JP | 6-198512 A | 7/1994 |
| TW | 577786 B | 3/2004 |

OTHER PUBLICATIONS

Taiwan Search Report, dated Aug. 18, 2013, from corresponding TW application.
International Search Report dated Aug. 11, 2008, from corresponding PCT application.

* cited by examiner

*Primary Examiner* — Will Fridie, Jr.
(74) *Attorney, Agent, or Firm* — Young & Thompson

(57) ABSTRACT

A rotating cutting tool (10, 110) includes a body (12, 112) with a longitudinal axis (14, 114) and at least one flute (16, 116) and one active part (18, 118). Each active part has a peripheral surface including: a radial cutting edge (20, 120) that is at a cutting distance (Rc) from the longitudinal axis, a clearance face (30, 130) that is at a final clearance distance (Rd) from the longitudinal axis, and a control face (40, 140) that is at a penetration control distance (Rp) from the longitudinal axis. These distances satisfy the relation:

$$0 < \Delta p < \Delta d, \text{ with } \Delta p = |Rc - Rp| \text{ and } \Delta d = |Rc - Rd|.$$

26 Claims, 9 Drawing Sheets

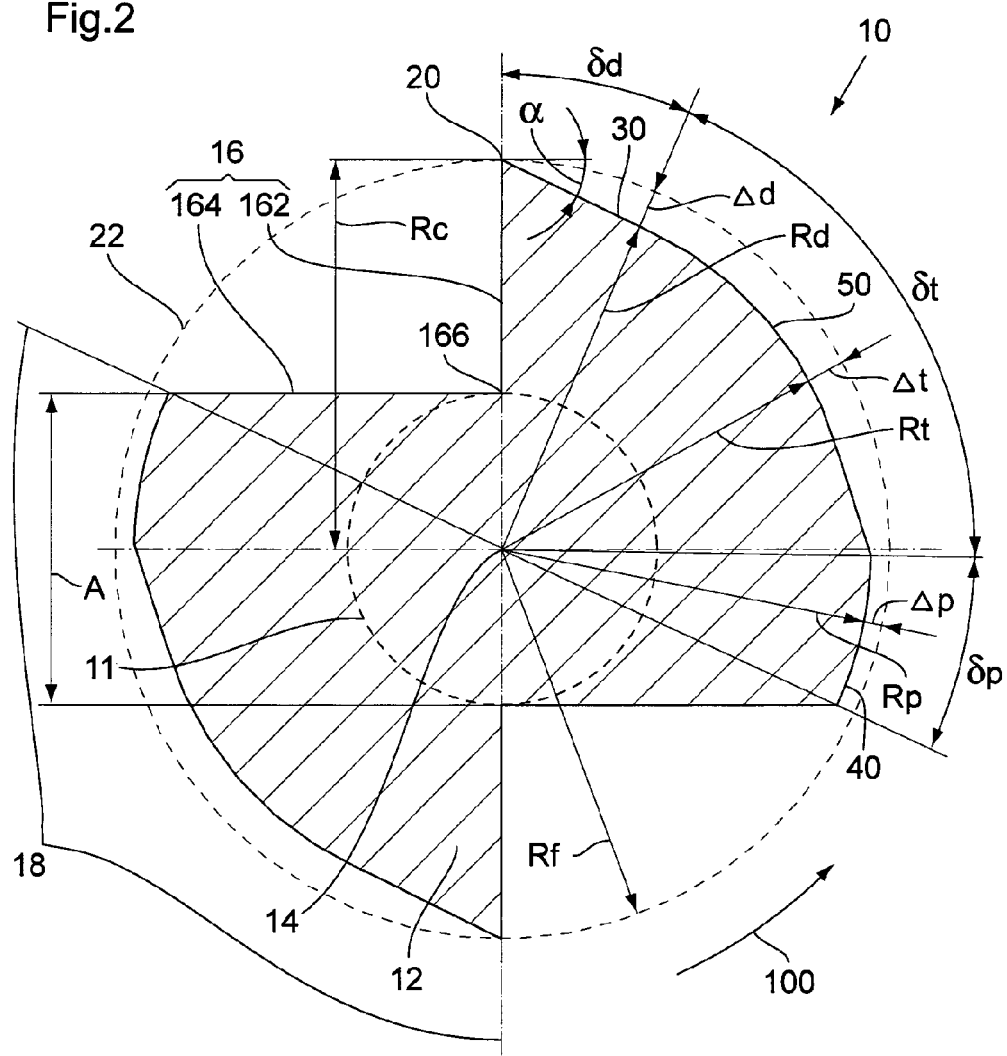

CUTTING INSTRUMENT AND METHODS FOR IMPLEMENTING SAME

The present invention relates to the field of cutting tools. It is aimed more particularly at a rotating cutting tool such as a milling cutter or drill. It is aimed as well at methods implementing such a cutting tool.

In the following outline, the term of "milling cutter" is used in the widest sense. It extends to borers as well as to the annular cutters that turn around a workpiece. In the following outline, such an annular cutter is called a "shell-type milling cutter", and a nonannular cutter is called a "solid-type milling cutter". In the following outline, the term of "longitudinal" refers to an entity substantially parallel to a longitudinal axis, while the term of "transverse" refers to an entity substantially perpendicular to this longitudinal axis.

A cutting tool according to the invention finds applications in numerous fields. A solid-type milling cutter can be used in the medical field, particularly in the dental field for endodontic treatments when boring root canals, shaping stumps, preparing and cutting crowns, and preparing cavities. A shell-type milling cutter can be used in the field of jewelery, for instance for the machining of setting claws. Though favoured, these applications are not limiting for the cutting tool according to the invention.

The dental field and the field of jewelery have in common that the elements to be machined or shaped—teeth or setting claws—have small dimensions and require a great precision of the machining operations. They have in common, too, that the technologies implemented for realising the cutting tools are similar.

The shaping of the cavities, false preprosthetic stumps, and prostheses is realised with milling cutters having highly varied geometries. These cutters can be round, cylindrical with a round end or a flat end, conical, ogival, etc. These cutters can have different diameters ranging from 0.6 mm to several millimeters. These cutters have several teeth, generally six. They have a cutting capacity that depends on their geometry.

An extended time of working with the cutting tool may lead to heating of the tool and of the material being machined, that is, of the dentine or prosthetic material. It will then be necessary to plan breaks for cooling that translate into a loss of time for the practician and reduced comfort for the patient being treated. An extended time of working may also lead to important wear of the cutting tool.

In the field of jewelery, the conditions of use are more particularly tied to the dimensions of the pieces being machined, and to the quality desired for the surfaces obtained after machining.

One already knows milling cutters of the solid type that are used in the dental field, and milling cutters of the shell type that are used in the field of jewelery.

These cutting tools exhibit an alternation of active parts and flutes. Every active part includes at least one radial cutting edge that attacks the material to be machined in a more or less aggressive way, generating chips of material removed. The chips are eliminated through a flute adjacent to the radial cutting edge.

It sometimes happens that the chips are not completely eliminated through the flutes, and get between the active part of the cutting tool and the material to be machined. These chips remain more or less mobile, or else aggregate in a particular region. In the field of endodonty where solid-type milling cutters are applied, chips get between the active part of the cutting tool and the wall of the root canal being cleaned, and may become lodged in recesses of the root canal. In the field of jewelery, where shell-type milling cutters are applied, the chips get between the active part of the cutting tool and the outer surface of the setting claw, and may remain mobile between these two parts. Chips not eliminated will in all cases perturb the machining operation. They may block the cutting tool or cause it to skid.

It is not always easy, moreover, to know at all times the true impact of the cutting tool on the material to be machined, and to proportion the power of the cutting tool, be it on the walls of teeth with a solid-type milling cutter or on the outside of a setting claw with a shell-type milling cutter.

It is one aim of the present invention to propose a cutting tool of the rotating type that could be used in particular in the dental field or another medical field, as well as in the field of jewelery, without being limited to that, and that overcomes the disadvantages mentioned hereinabove.

SUMMARY OF THE INVENTION

According to a first aspect, the invention refers to a cutting tool of the rotating type, and in particular a milling cutter or borer, said cutting tool being provided with a body having a longitudinal axis and at least one flute alternating with at least one active part. According to the invention, every active part has a peripheral surface comprising in succession:
  a radial cutting edge,
  a clearance face to favour elimination of the chips, and
  a control face to control the depth of penetration of the cutting, said control face opening into a flute,
  and
  said radial cutting edge defines a cutting envelope and is situated at a cutting distance Rc from said longitudinal axis,
  said clearance face is defined by an angular clearance length and is situated at a distance from said longitudinal axis that varies between the cutting distance Rc and a final clearance distance Rd,
  said control face is defined by an angular penetration control length and is situated at a penetration control distance Rp from said longitudinal axis, and
  the absolute difference $\Delta p$ between said cutting distance Rc and said penetration control distance Rp is larger than zero, and smaller than the absolute difference $\Delta d$ between said cutting distance Rc and said final clearance distance Rd, satisfying the relation:

$$0<\Delta p<\Delta d, \text{ with } \Delta p=|Rc-Rp| \text{ and } \Delta d=|Rc-Rd|.$$

An advantage of such a cutting tool resides in the fact that for every active part, the radial cutting edge constitutes the only zone of the peripheral surface of the active part that reaches the cutting envelope.

According to a first variant of realisation that corresponds to a cutting tool of the solid type, the clearance face extends from the radial cutting edge while getting closer to the longitudinal axis of the body up to a final clearance distance. According to a second variant of realisation that corresponds to a cutting tool of the shell type, the clearance face similarly extends from the radial cutting edge while departing from the longitudinal axis of the body up to a final clearance distance.

For the two variants of realisation, the control face extends at a distance that lies between the cutting distance and the final clearance distance. It follows that chips that have not been eliminated into the flute preceding the radial cutting edge in the direction of rotation of the cutting tool, can be conveyed along the clearance face and then along the control face up to the following flute, where they can remain prior to being eliminated. The danger of chips stuck in front of active parts is strongly reduced if not suppressed. The control face moreover allows one to measure or impose with precision a minimum distance of penetration of the radial cutting edge into the workpiece. Lastly, the fact that the penetration control distance has a value between the cutting distance and the final clearance distance, allows one to significantly reduce the vibrations during cutting.

According to the first variant of realisation, the body is a cylindrical or conical or rounded-shaped body, with a radius that coincides with the cutting distance.

According to a characteristic of this first variant of realisation, the free end of said body comprises protruding front edges where each front edge substantially extends up to the longitudinal median plane that is perpendicular to it, and wherein at least one of said front edges extends beyond said longitudinal median plane that is perpendicular to it. An advantage of this characteristic resides in the fact that the free end of the cutting tool is given an additional function. With the "solid-type" cutting tools known until now, the central part of the free end only serves to pierce the material to be machined. According to the invention, when at least one front edge extends beyond the longitudinal median plane that is perpendicular to it, the central part of the free end becomes a zone that not only pierces but also cuts. According to an additional characteristic of this first variant of realisation, each of these front edges is situated in the longitudinal extension of a flute wall on which a radial cutting edge is resting.

According to the second variant of realisation, the body is an annular body with a cylindrical or conical or rounded shape, and having an inner radius that coincides with the cutting distance.

Particular embodiments of the cutting tool according to the first aspect of the invention are defined in the appended claims 2 to 5, 7 to 13, 16, 17, and 19 to 24.

According to a second aspect, the invention relates to methods applying a cutting tool according to the first aspect of the invention, and in particular:
- a method of preparing a root canal during an endodontic treatment that applies a cutting tool according to the first variant of the first aspect of the invention,
- a method of machining of a setting claw in the field of jewelery that applies a cutting tool according to the second variant of the first aspect of the invention.

BRIEF DESCRIPTION OF THE DRAWINGS

The invention will be better understood when reading the following detailed description of particular embodiments of the cutting tool that are provided as an illustration and are by no means limiting, while referring to the annexed drawings where:

FIG. 2 represents a transverse section of the cutting tool of FIG. 1;

First a solid-type milling cutter will be described as cutting tool 10 while referring to FIGS. 1 to 13. FIG. 1 represents in perspective a cutting tool 10 with a body 12 assembled on a shank 13 integral with a drive shaft 3. Body 12 is a cylindrical or conical body or a body having a rounded form, of revolution about a longitudinal axis 14. By rounded form, a shape is understood that in longitudinal section has an envelope of non-rectilinear profile. Such a rounded form could for example be a spherical, pear, barrel, or flame shape. Body 12 is provided with two straight flutes 16 and two active parts 18 alternating with these flutes 16. Body 12 terminates in a free end 90 that will be described in detail later.

DETAILED DESCRIPTION OF THE DRAWINGS

Figure 1:
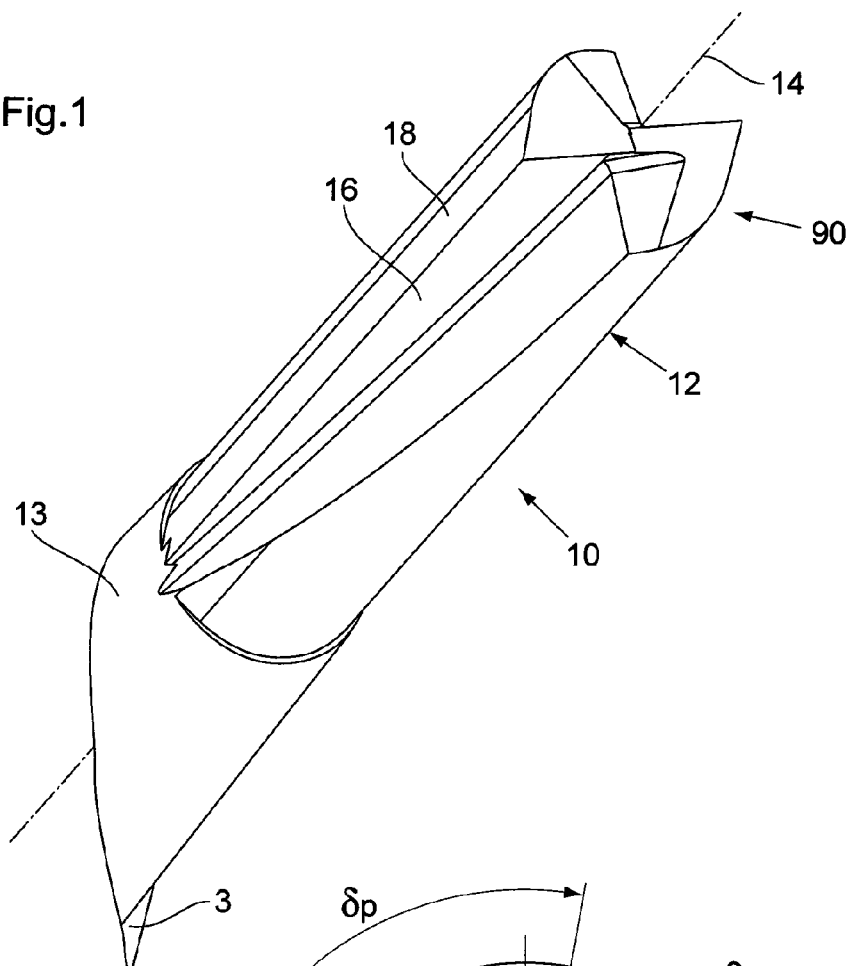
FIG. 1 represents in perspective a "solid-type" milling cutter having two flutes and two active parts.

A transverse section of the cutting tool 10 of FIG. 1 is represented in FIG. 2. This transverse section has central symmetry.

Each flute 16 is delimited by two walls 162, 164, both flat and mutually perpendicular so that the bottom 166 of the flute 16 defines a right angle.

Core 11 of body 12 is defined as the central part of the body that is inside a cylinder or cone or rounded form centred on the longitudinal axis 14, and delimited by the bottoms 166 of flutes 16. This core 11 of body 12 has a diameter indicated by letter A in FIG. 2. Diameter A is a percentage of the diameter of body 12 comprised between 0% and 95% of that diameter, preferably between 5% and 30%, and even more preferably between 10% and 20%.

Figure 3:
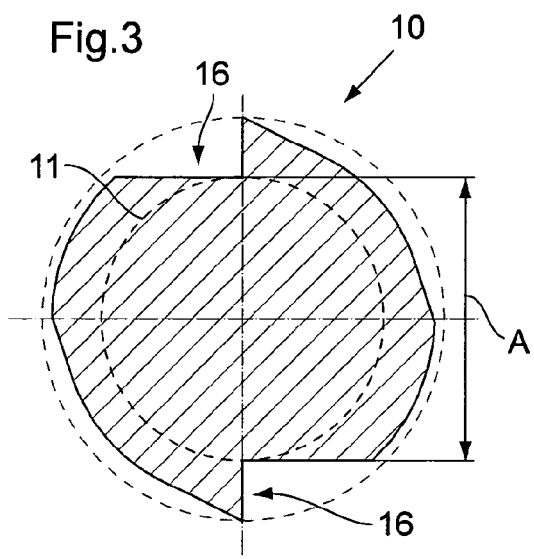
FIGS. 3 and 4 are analogues of FIG. 2 illustrating the size range of the cutting tool's core, as well as the volume range of the flutes.
Figure 4:
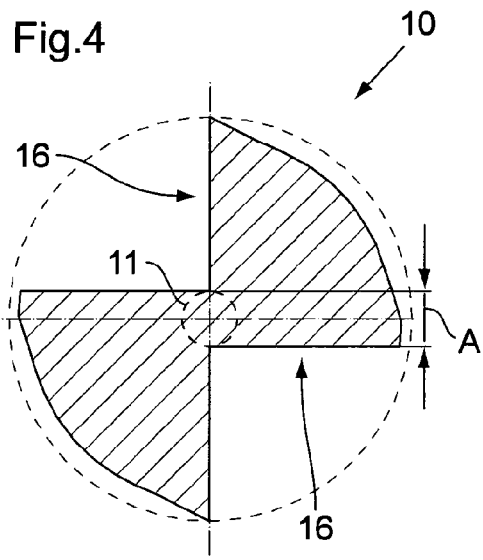

FIGS. 3 and 4 both represent a transverse section of a cutting tool 10 analogous to that of FIG. 2, illustrating the size range of core 11 of body 12 as well as the volume range of the flutes 16. FIG. 3 shows the maximum value that can be attained by core 11 of cutting tool 10, and the minimum value of the volume of the flutes 16, while FIG. 4 shows the minimum value that can be attained by core 11 of cutting tool 10, and the maximum value of the volume of the flutes 16.

Returning to FIG. 2, it appears that the peripheral surface of each active part 18 comprises in succession: a radial cutting edge 20, a clearance face 30, and a control face 40, as well as a transition face 50 extending between the clearance face 30 and the control face 40.

The radial cutting edge 20 is at a distance Rc, so-called cutting distance, from the longitudinal axis 14. It defines a cylindrical or conical or rounded cutting envelope 22 which has a radius equal to the cutting distance Rc and which is represented in FIG. 2 by a circle in broken lines. The cutting distance Rc coincides with radius Rf of body 12.

The radial cutting edge 20 rests on one of the walls of flute 16, more precisely on wall 162 which precedes it in the direction of rotation of cutting tool 10 that is indicated by arrow 100 in the figures.

Figure 5:
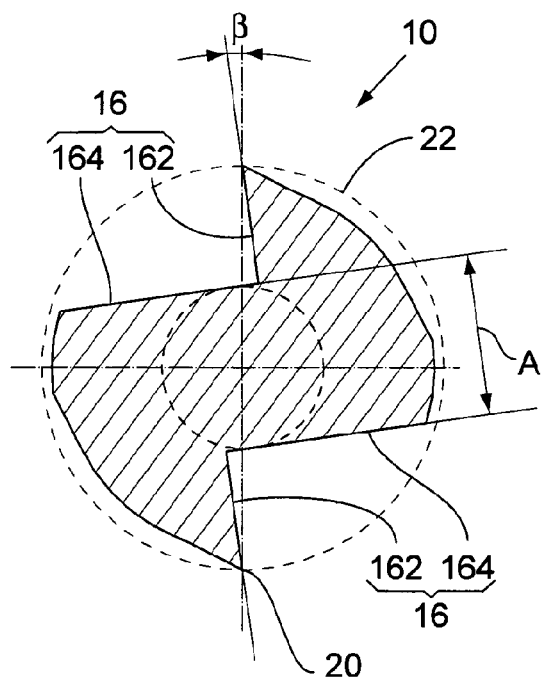
FIGS. 5 and 6 are analogues of FIG. 2 illustrating the range of values of the angle of attack of the cutting tool's radial cutting edge.
Figure 6:
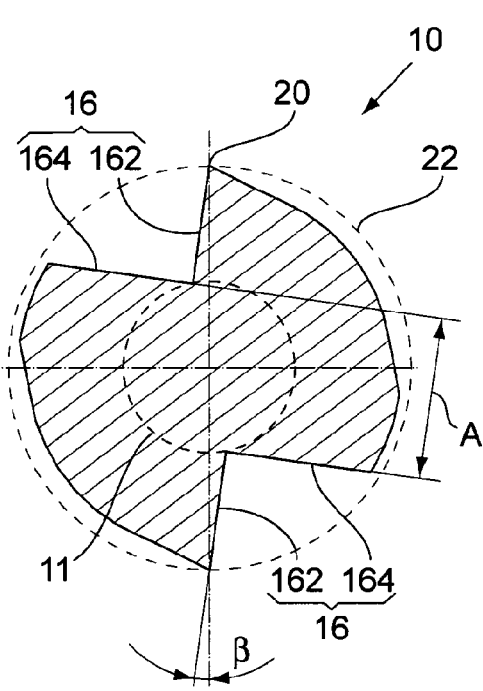

When this wall 162 is borne by a radius Rf of body 12 as shown in FIG. 2, then the radial cutting edge 20 has an angle of attack β that is substantially zero. When this wall 162 departs from a radius of body 12 in the direction from the radial cutting edge 20 toward the active part 18 as represented in FIG. 5, then the radial cutting edge 20 has a negative angle of attack β. When this wall 162 departs from a radius of body 12 in the direction from the radial cutting edge 20 toward flute 16 as represented in FIG. 6, then the radial cutting edge 20 has a positive angle of attack β.

This angle of attack β is comprised between −45° and 45°, preferably between −20° and 20°, and even more preferably between −10° and 10°.

According to the invention it is preferred that the angle of attack β be negative, of by default zero, so that cutting tool 10 will show commensurate aggressiveness of cutting.

Coming back to FIG. 2, the clearance face 30 extends from the radial cutting edge 20 in the direction opposite to that of rotation 100 of the cutting tool 10. This clearance face 30 is a substantially flat face defined by a clearance angle α and by an angular clearance length δd. It is at a distance from the longitudinal axis 14 that varies between the cutting distance Rc at its end abutting the radial cutting edge 20, and a final clearance distance Rd at its opposite end.

The clearance angle α is the angle formed between this clearance face 30 and the plane that is tangent to the cutting envelope 22, and having the radial cutting edge 20 as its apex. This clearance angle α is comprised between 0° and 45°, preferably between 5° and 30° and even more preferably between 10° and 20°.

The angular clearance length δd is the angle of the sector that is centred on the longitudinal axis 14 and delimits the clearance face 30. This angular clearance length δd is comprised between 5° and 160°, preferably between 6° and 50° and even more preferably between 7° and 10°.

The angular length δd of this clearance face 30 depends on the grinding wheel used to machine the cutting tool 10, and on the diameter and shape of said cutting tool 10. The final clearance distance Rd is a function of the clearance angle α and of the angular clearance length δd.

Since the cutting tool 10 is a solid-type milling cutter, and has a transverse section inscribed into a disc, then the final clearance distance Rd is smaller than the cutting distance Rc. It follows that the absolute difference Δd between the cutting distance Rc and the final clearance distance Rd represents the radial distance between the cutting envelope 22 and the peripheral surface of the active part 18 at the end of the clearance face 30. This absolute difference Δd is comprised between 0.03 mm and 0.3 mm.

A transition face 50 that will be described in greater detail in the following, extends from the clearance face 30, still in the direction opposite to that of rotation 100 of cutting tool 10.

The control face 40 that is defined by an angular penetration control length δp, and is at a distance Rp, so-called penetration control distance, from the longitudinal axis 14, extends from the transition face 50, still in the direction opposite to that of rotation 100 of cutting tool 10.

The angular penetration control length δp is the angle of the sector centred on the longitudinal axis 14 that delimits the control face 40. This angular penetration control length δp is comprised between 0° and 100°, preferably between 5° and 60°, and even more preferably between 10° and 30°.

The angular length δp of this control face 40 depends on the cutting capacity, on the size of the grinding wheel used to machine the cutting tool 10, and on the dimensions of said cutting tool 10.

A first form of realisation of said control face 40 for which the penetration control distance Rp is constant so that said control face 40 exhibits a profile of substantially a circular arc in a plane transverse to said longitudinal axis 14, is illustrated in FIG. 2.

The absolute difference Δp between the cutting distance Rc and the penetration control distance Rp represents the radial distance between the cutting envelope 22 and the peripheral surface of the active part 18 along the control face 40. This absolute difference Δp is comprised between 0.03 mm and 0.3 mm.

Figure 7:
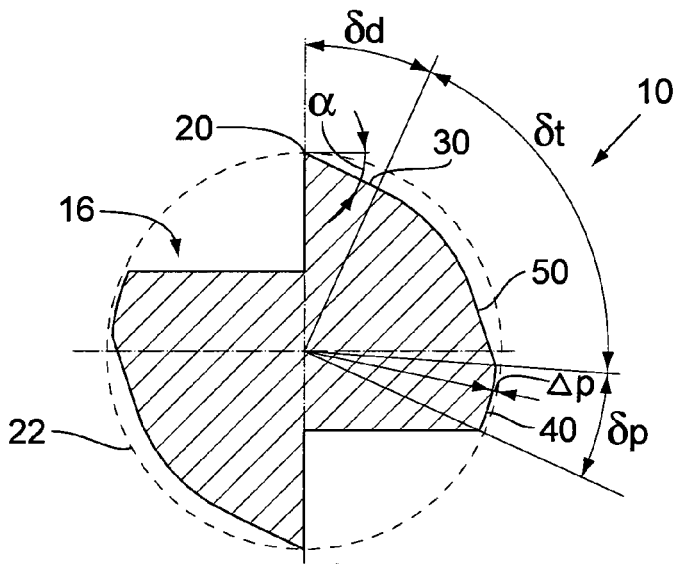
FIGS. 7 and 8 are analogues of FIG. 2 illustrating the range of values of the cutting tool's penetration control distance.
Figure 8:
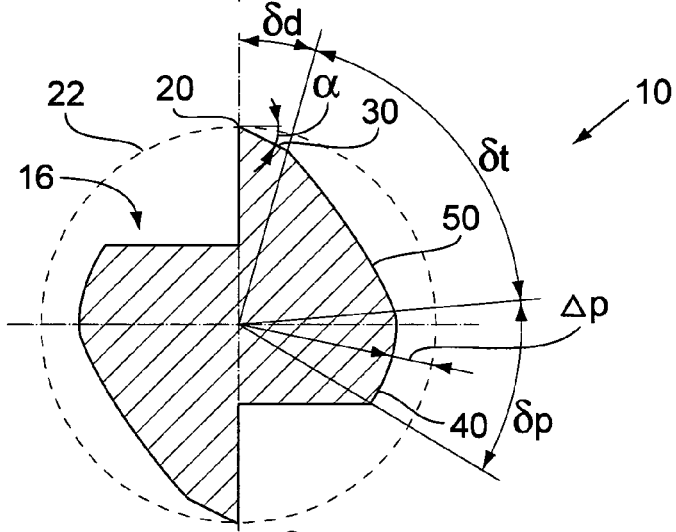

FIGS. 7 and 8 both represent a transverse section of a cutting tool 10 analogous to that of FIG. 2 and illustrate the range of values of this difference Δp. FIG. 7 shows the minimum value of this difference Δp, while FIG. 8 shows the maximum value of this difference Δp.

Figure 9:
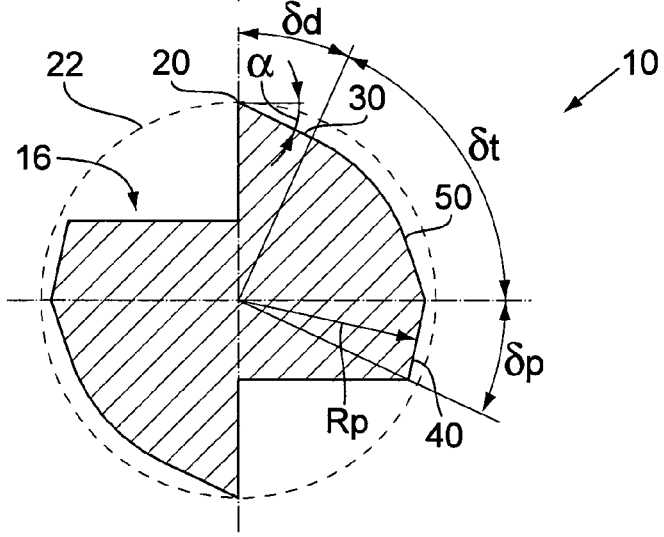
FIG. 9 is an analogue of FIG. 2 illustrating a geometrical variant of the control face.

FIG. 9 illustrates a second form of realisation of said control face 40 that is a substantially flat face for which the penetration control distance Rp is not constant, so that said control face 40 in a plane transverse to said longitudinal axis 14 has a substantially rectilinear profile. Preferably this rectilinear profile substantially corresponds to the chord of the circular-arc profile of the variant illustrated in FIG. 2.

According to a characteristic of the first variant of realisation of the cutting tool 10 the cutting distance Rc, the final clearance distance Rd and the penetration control distance Rp satisfy the relation: Rd<Rp<Rc.

More particularly, the difference between the cutting distance Rc and the penetration control distance Rp is greater than zero and smaller than the difference between the cutting distance Rc and the final clearance distance Rd, which translates to the relation: 0<Rc−Rp<Rc−Rd.

Said otherwise, the absolute difference between the cutting distance Rc and the penetration control distance Rp is different from zero, and smaller than the absolute difference between the cutting distance Rc and the final clearance distance Rd, which translates to the relation:

$$0<\Delta p<\Delta d, \text{ with } \Delta p=|Rc-Rp| \text{ and } \Delta d=|Rc-Rd|.$$

Returning now to FIG. 2, the transition face 50 will be described. This transition face 50 is defined by an angular transition length δt, and is at a distance Rt, so-called transition distance, from the longitudinal axis 14.

The angular transition length δt is the angle of the sector centred on the longitudinal axis 14 that delimits the transition face 50. It is comprised between 0° and 150°, preferably between 30° and 120°, and even more preferably between 60° and 90°.

The transition face 50 serves to link the clearance face 30 and the control face 40. Preferably, the transition face 50 has a generally convex contour. In the example illustrated in FIG. 2, the transition face 50 has, in transverse section, a contour consisting of a central part in the shape of a circular arc substantially concentric with the cutting envelope 22, and of two terminal parts situated to both sides of the central part. These two terminal parts are more or less long, and progressively link the central part with the clearance face 30 and the control face 40 that are situated to both sides of this transition face 50.

The value of the transition distance Rt has no particular significance, since the only function of transition face 50 is that of linking the clearance face 30 and the control face 40. It is only important that the penetration control distance Rp remain larger than this transition distance Rt, and satisfy the relation: Rt<Rp<Rc. Said otherwise, the absolute difference Δp between the cutting distance Rc and the penetration control distance Rp remains smaller than the absolute difference Δt between the cutting distance Rc and the transition distance Rt, satisfying the relation:

$$0<\Delta p<\Delta t, \text{ with } \Delta p=|Rc-Rp| \text{ and } \Delta t=|Rc-Rt|.$$

An advantage of this arrangement (Δp<Δt) resides in the fact that the chips that might not have been eliminated into the flute 16 preceding the radial cutting edge 20 may easily be conveyed between the clearance face 30 and the control face 40 without being retained or slowed down in whatever way at the transition face 50.

Figure 10:
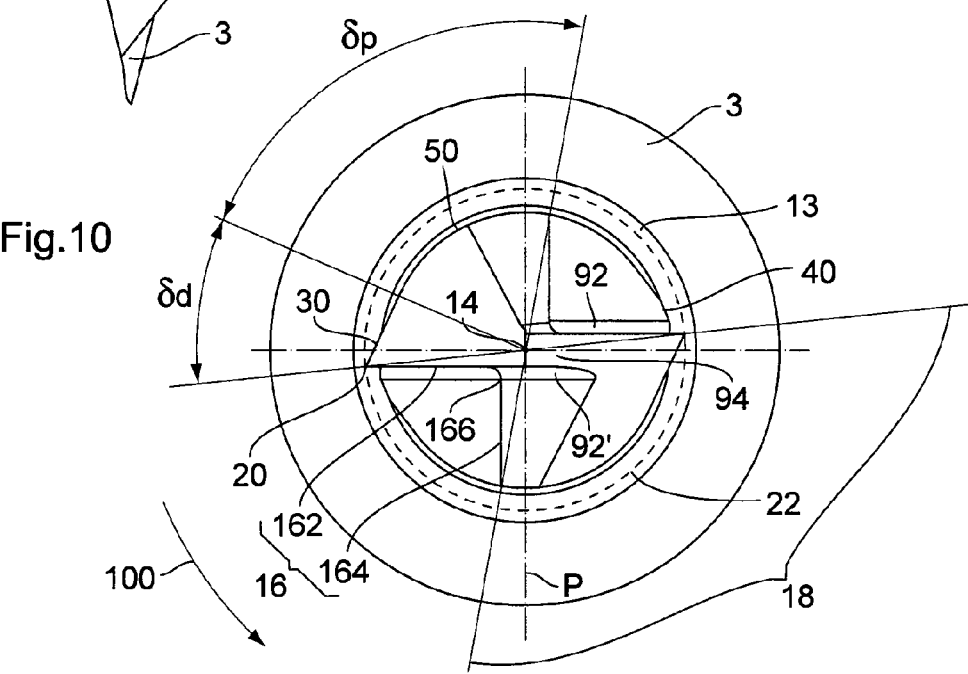
FIG. 10 represents the free end of the cutting tool in a front view.

The free end 90 of the cutting tool 10 of FIG. 1 is illustrated in FIG. 10 in a front view. The two radial cutting edges 20 define the cutting envelope 22. The clearance face 30 is followed by a transition face 50 that in turn is followed by a control face 40. Each flute 16 is delimited by two walls 162, 164 mutually substantially perpendicular and meeting at the bottom 166 of flute 16. Each radial cutting edge 20 rests on wall 162 of the flute 16 preceding it in the direction of rotation 100 of cutting tool 10. Each of these walls 162 is extended forward, along the direction of the longitudinal axis 14, by a front edge 92, 92'. A longitudinal median plane perpendicular to the two edges 92, 92' is indicated by letter P. Considering the upper part of FIG. 10, the front edge 92 substantially extends up to the longitudinal median plane P. Considering the lower part of FIG. 10, the other front edge 92' extends beyond this longitudinal median plane P. It follows that a substantially central zone 94 of free end 90 of the cutting tool 10 exists that is a zone of overlap between these two front edges 92, 92'. In the example illustrated, this overlap zone 94 is on only one side (the right-hand side in FIG. 10) of the longitudinal median plane P. In a variant, the overlap zone 94 could be on both sides of this longitudinal median plane P, while the free end 90 would have its two edges 92, 92' extending beyond the longitudinal median plane P, but the configuration of FIG. 10 is preferred.

It appears that the cutting will be more efficient the larger the number of front edges extending beyond the longitudinal median plane that is perpendicular to them. However, if the number of such front edges is too large, the central part of the free end becomes fragile, which may cause one or several edges to break. This is why it is preferable to limit the number of edges concerned. For instance, when the free end of the cutting tool has exactly two front edges, it is preferable that only one of these two edges extend beyond the longitudinal median plane perpendicular to it. This is the example illustrated in FIG. 10.

Figure 11:
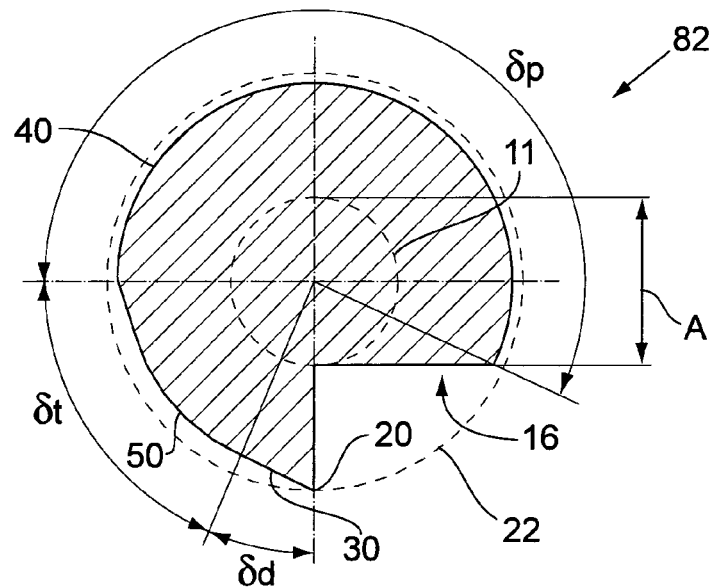
FIGS. 11, 12 and 13 are analogues of FIG. 2 for cutting tools having one flute and one active part, three flutes and three active parts, or four flutes and four active parts, respectively.
Figure 12:
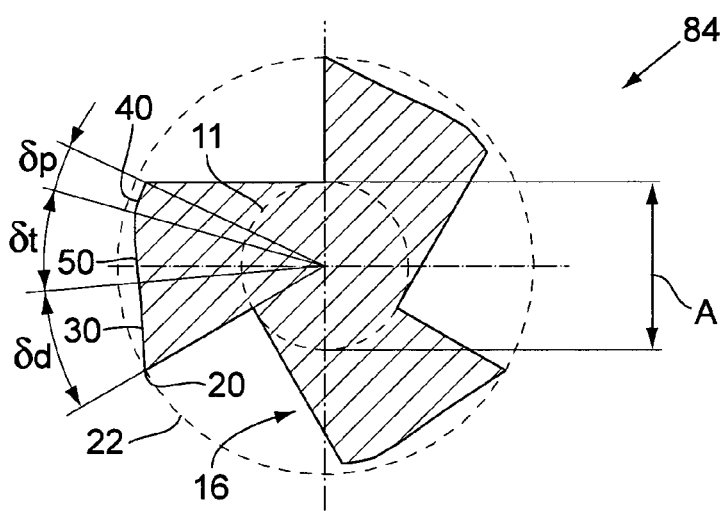
Figure 13:
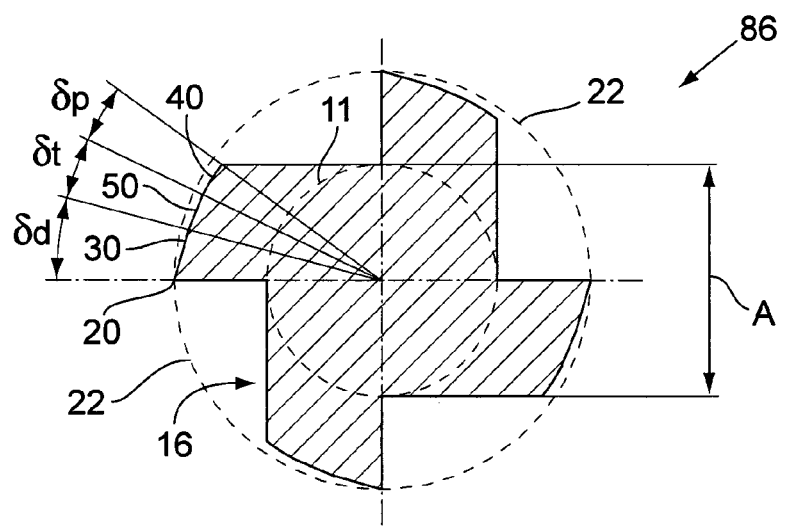

FIGS. 11, 12, and 13 illustrate alternative embodiments of the cutting tool 82, 84, 86 that differ from the cutting tool 10 illustrated in FIG. 2 by the number of flutes 16 and active parts 18 that they have. The cutting tool 82 illustrated in FIG. 11 has one flute 16 and one active part 18. In this case the angular penetration control length δp is comprised between 0 and 300°. The cutting tool 84 illustrated in FIG. 12 has three flutes 16 and three active parts 18. The cutting tool 86 illustrated in FIG. 13 has four flutes 16 and four active parts 18. Their other characteristics are analogous to those described while referring to FIGS. 1 to 10.

A cutting tool 10 corresponding to the first variant of realisation that has just been described while referring to FIGS. 1 to 13 can be applied in a method of preparing a root canal during dental treatment. Such a cutting tool 10 is preferably made of tungsten carbide, martensitic stainless steel, or carbon steel.

A shell-type milling cutter will now be described as a cutting tool 110 while referring to FIGS. 14 to 23.

Figure 14:
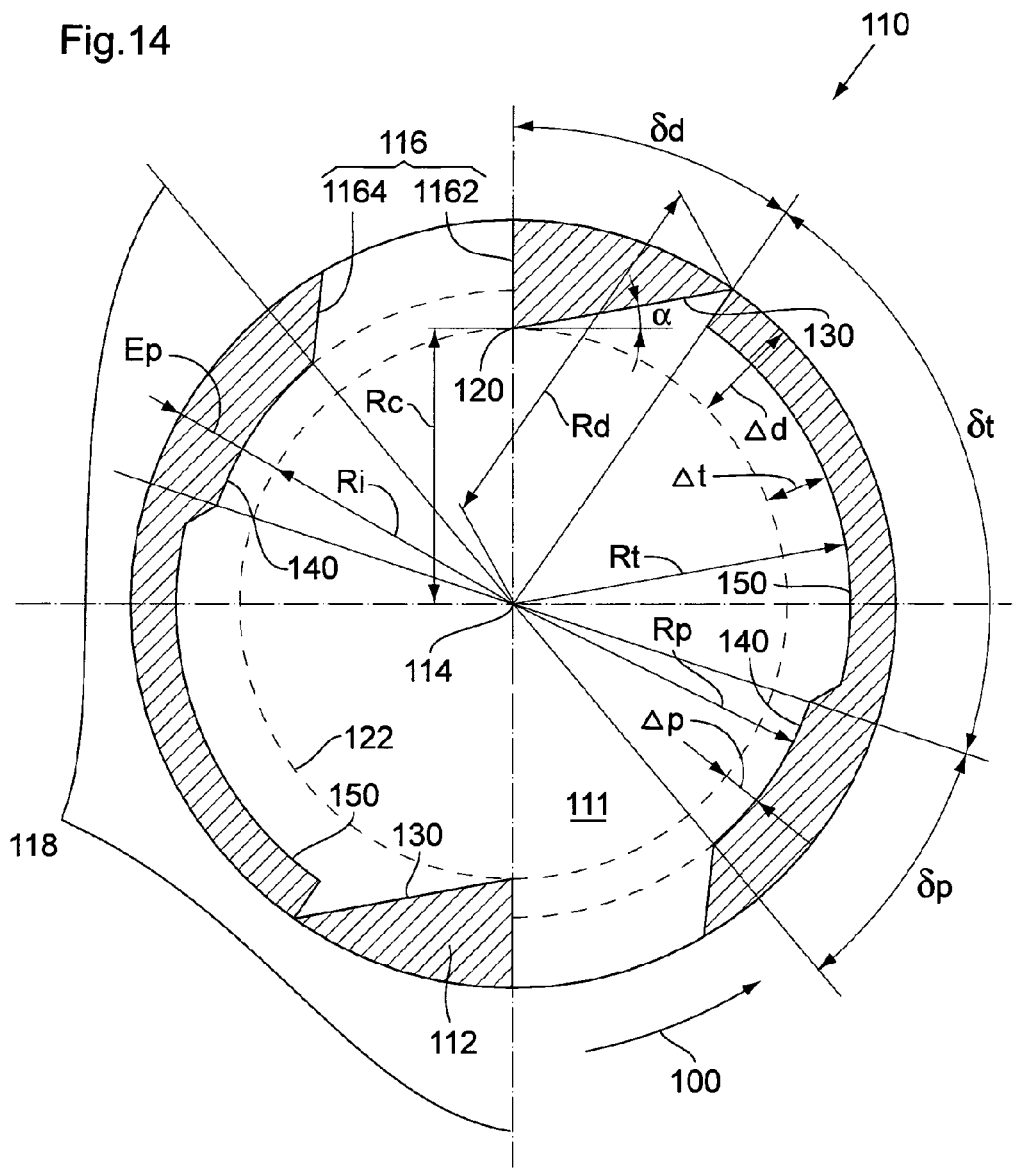
FIG. 14 represents a "shell-type" cutting tool having two flutes and two active parts, in a transverse section.

FIG. 14 represents a transverse section of a cutting tool 110 including a hemispherical calotte 111 that is extended by an annular body 112 that is cylindrical or conical, or of a rounded form, of revolution about a longitudinal axis 114. This transverse section has central symmetry. Body 112 is provided with two helical flutes 116 and two helical active parts 118 alternating with these flutes 116. It has an inner radius Ri and a thickness Ep.

Still in FIG. 14, the peripheral surface of each active part 118 comprises in succession: a radial cutting edge 120, a clearance face 130, and a control face 140, as well as a transition face 150 extending between the clearance face 130 and the control face 140.

Figure 15:
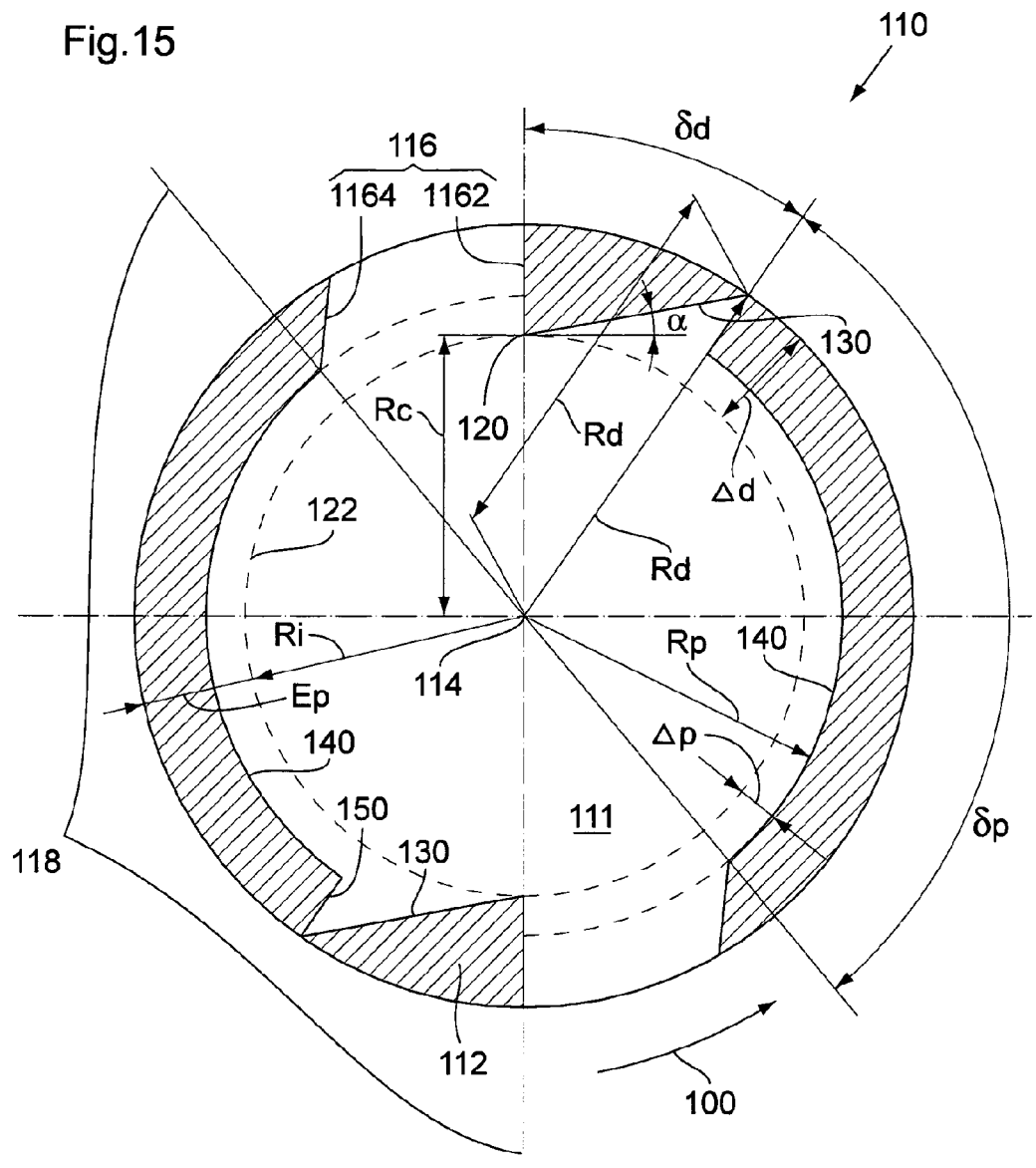
FIG. 15 illustrates an alternative form of realisation of the cutting tool of FIG. 14.

Referring to FIG. 15, a transverse section of an alternative form of realisation of the cutting tool of the type of a shell-type milling cutter is represented, where the transition face 150 is reduced to a purely radial face.

The radial cutting edge 120 is at a distance Rc, so-called cutting distance, from the longitudinal axis 114. It defines a cylindrical or conical or rounded cutting envelope 122, of annular shape, represented by a circle in broken lines in FIGS. 14 and 15.

The radial cutting edge 120 rests on one of the walls of flute 116, more precisely on wall 1162 which precedes it in the direction of rotation of cutting tool 110 that is indicated by arrow 100 in the figures.

Figure 16:
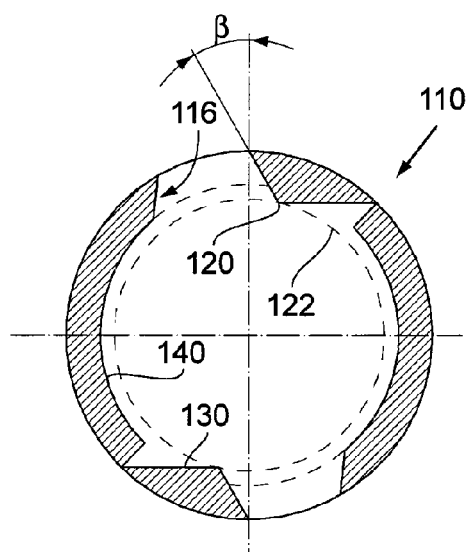
FIGS. 16 and 17 are analogues of FIG. 15 illustrating the range of values of the cutting tool's angle of attack.
Figure 17:
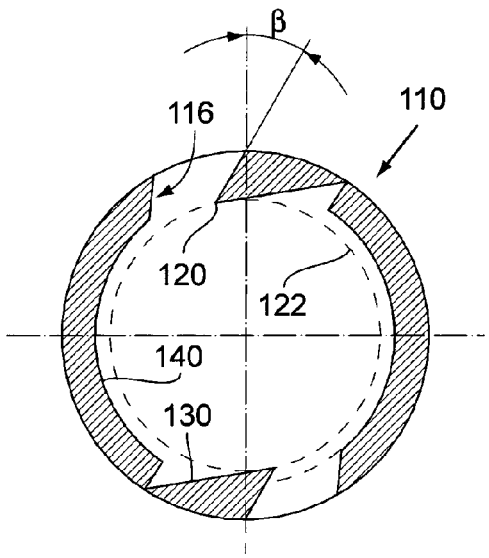

When this wall 1162 is borne by a radius of body 112 as shown in FIGS. 14 and 15, then the radial cutting edge 120 has an angle of attack β that is substantially zero. When this wall 1162 departs from a radius of body 112 in the direction from the radial cutting edge 120 toward the active part 118 as represented in FIG. 16, then the radial cutting edge 120 has a positive angle of attack β. When this wall 1162 departs from a radius of body 112 in the direction from the radial cutting edge 120 toward flute 116 as represented in FIG. 17, then the radial cutting edge 120 has a negative angle of attack β.

This angle of attack β is comprised between −45° and 45°, preferably between −20° and 20°, and even more preferably between −10° and 10°.

According to the invention it is preferred that the angle of attack β be negative, of by default zero, so that cutting tool 110 will show commensurate aggressiveness of cutting.

Coming back to FIGS. 14 and 15, the clearance face 130 extends from the radial cutting edge 120 in the direction opposite to that of rotation of cutting tool 110. This clearance face 130 is a substantially flat face defined by a clearance angle α and by an angular clearance length δd. It is at a distance from the longitudinal axis 114 that varies between the cutting distance Rc at its end abutting the radial cutting edge 120 and a final clearance distance Rd at its opposite end.

The clearance angle α is the angle formed between this clearance face 130 and the plane that is tangent to the cutting envelope 122, and having the radial cutting edge 120 as its apex. This clearance angle α is comprised between 0° and 30°, preferably between 5° and 25° and even more preferably between 10° and 20°.

The angular clearance length δd is the angle of the sector that is centred on the longitudinal axis 114 and delimits the clearance face 130. This angular clearance length δd is comprised between 10° and 90°, preferably between 20° and 60° and even more preferably between 30° and 45°.

Figure 18:
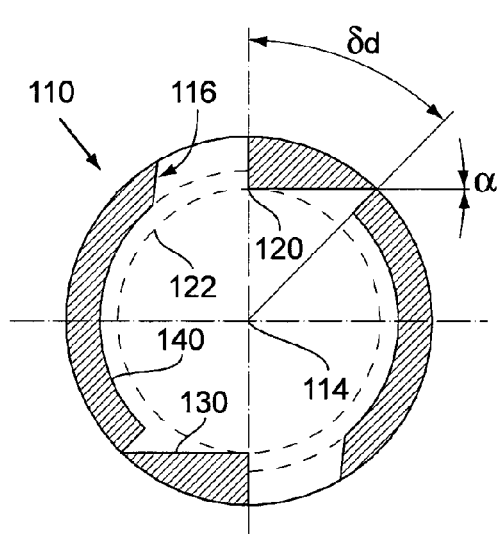
FIGS. 18 and 19 are analogues of FIG. 15 illustrating the range of values of the cutting tool's angular clearance length.
Figure 19:
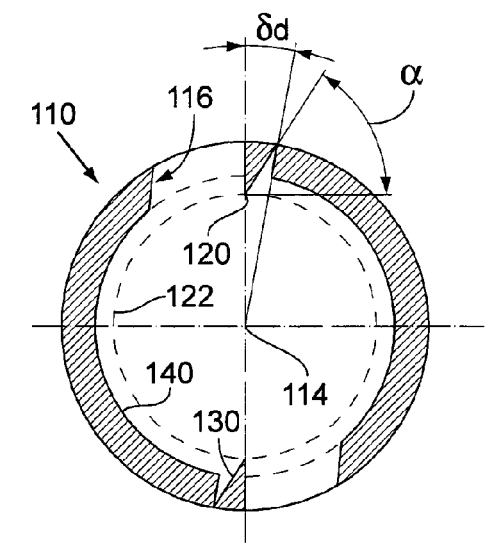

FIGS. 18 and 19 both represent a transverse section of a cutting tool 110 analogous to that of FIG. 15, illustrating the range of values of the angular clearance length δd. FIG. 18 shows the maximum value that can be attained by the angular clearance length δd, while FIG. 19 shows the minimum value that can be attained by the angular clearance length δd.

The angular length δd of this clearance face 130 depends on the size of the milling cutter used to machine the cutting tool 110, and on the diameter of said cutting tool 110. The final clearance distance Rd is a function of the clearance angle α and of the angular clearance length δd.

The final clearance distance Rd is larger than the cutting distance Rc, since the cutting tool 110 is a shell-type milling cutter and has a transverse section inscribed into a ring. It follows that the absolute difference Δd between the cutting distance Rc and the final clearance distance Rd represents the radial distance between the cutting envelope 122 and the peripheral surface of the active part 118 along this clearance face 130. This absolute difference Δd is a percentage of the outer radius that is defined as the sum of inner radius Ri and thickness Ep of the annular body 112. The absolute difference Δd is comprised between 2% and 15% of the outer radius, and preferably substantially equal to 7% of said outer radius.

A transition face 150 that will be described in greater detail in the following while referring to both FIGS. 14 and 15 extends from the clearance face 130, still in the direction opposite to that of rotation 100 of the cutting tool 110.

The control face 140 that is defined by an angular penetration control length δp, and that is at a distance Rp, so-called penetration control distance, from the longitudinal axis 114, extends from the transition face 150, still in the direction opposite to that of rotation 100 of the cutting tool 110.

The angular penetration control length δp is the angle of the sector centred on the longitudinal axis 114 that delimits the control face 140. This angular penetration control length δp is comprised between 60° and 140°, preferably between 75° and 130° and even more preferably between 90° and 120°.

The angular control length δp of this control face 140 depends on the cutting capacity, on the size of the grinding wheel or milling cutter used to machine the cutting tool 110, and on the dimensions of said cutting tool 100.

Figure 20:
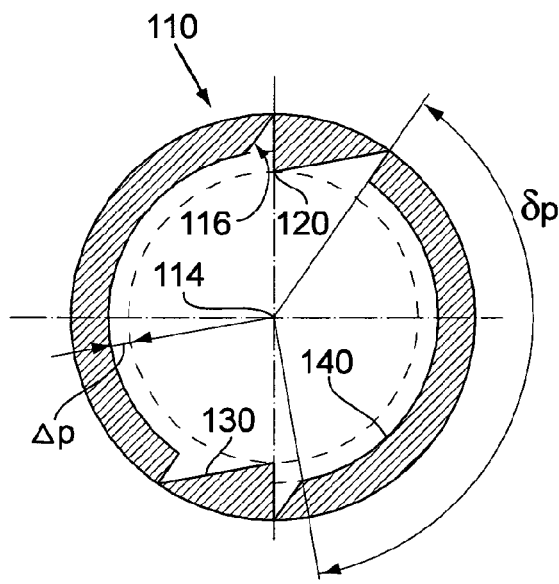
FIGS. 20 and 21 are analogues of FIG. 15 illustrating the range of values of the angular control length as well as the range of flute volumes of the cutting tool.
Figure 21:
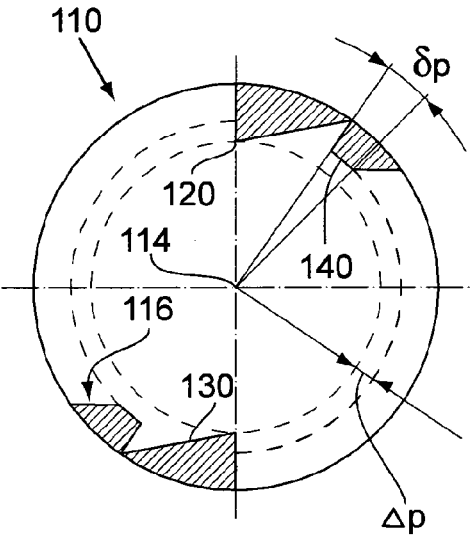

FIGS. 20 and 21 both represent a transverse section of a cutting tool 110 analogous to that of FIG. 15 illustrating the range of values of said angular control length δp. FIG. 20 shows the maximum value that can be attained by this angular penetration control length δp, while FIG. 21 shows the minimum value that can be attained by the angular penetration control length δp.

In the example illustrated in FIGS. 14 to 23, the penetration control distance Rp is constant, so that said control face 140 has a profile that in a plane transverse to the longitudinal axis 114 is substantially a circular arc.

The absolute difference Δp between the cutting distance Rc and the penetration control distance Rp represents the radial distance between the cutting envelope 122 and the peripheral surface of the active part 118 along this control face 140. This absolute difference Δp is comprised between 0.03 mm and 0.3 mm.

Figure 22:
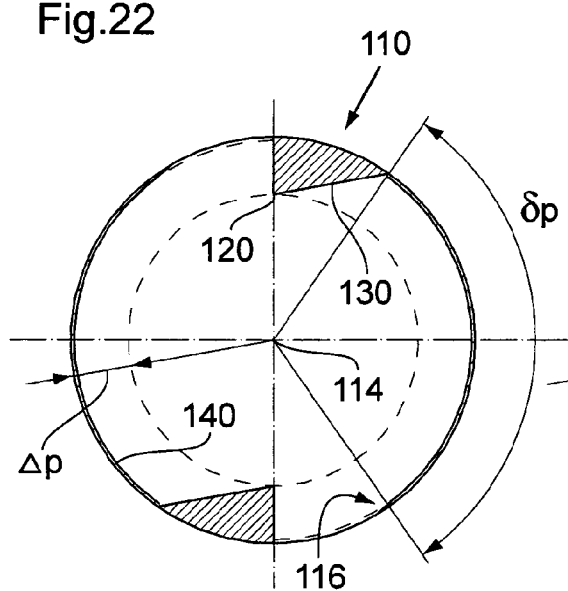
FIGS. 22 and 23 are analogues of FIG. 15 illustrating the range of values of the cutting tool's control distance.
Figure 23:
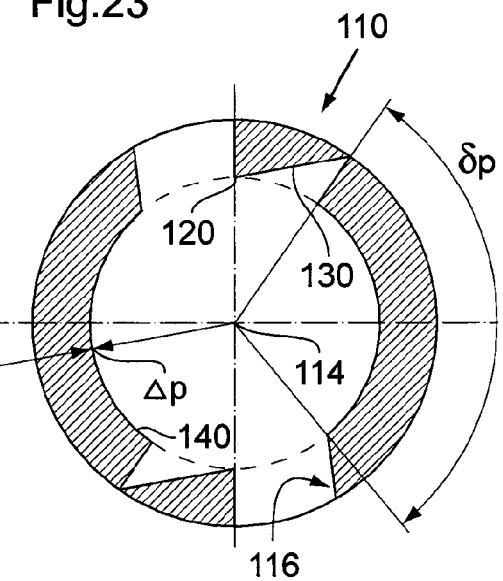

FIGS. 22 and 23 both represent a transverse section of a cutting tool 110 analogous to that of FIG. 15 illustrating the range of values of this difference Δp. FIG. 22 shows the maximum value that can be attained by this difference Δp, while FIG. 23 shows the minimum value that can be attained by this difference Δp.

According to a characteristic of the second variant of realisation of the cutting tool 110 the cutting distance Rc, the final clearance distance Rd, and the penetration control distance Rp satisfy the relation: Rc<Rp<Rd.

More particularly, the difference between the penetration control distance Rp and the cutting distance Rc is greater than zero and smaller than the difference between the final clearance distance Rd and the cutting distance Rc, which translates to the relation: 0 <Rp−Rc<Rd−Rc.

Said otherwise, the absolute difference between the cutting distance Rc and the penetration control distance Rp is different from zero, and smaller than the absolute difference between the cutting distance Rc and the final clearance distance Rd, which translates to the relation:

$$0<\Delta p<\Delta d, \text{ with } \Delta p=|Rc-Rp| \text{ and } \Delta d=|Rc-Rd|.$$

Returning now to FIGS. 14 and 15, the transition face 150 will be briefly described. This transition face 150 is defined by an angular transition length δt and is at a distance Rt, so-called transition distance, from the longitudinal axis 114.

In the example illustrated in FIG. 14, the angular transition length δt is the angle of the sector centred on the longitudinal axis 114 that delimits the transition face 150. It is comprised between 0° and 150°, preferably between 30° and 120° and even more preferably between 60° and 90°.

Preferably, the transition face 150 has a generally concave contour. In the example illustrated in FIG. 14, the transition face 150 has, in transverse section, a contour consisting of a central portion in the shape of a circular arc substantially concentric with the cutting envelope 122, a purely radial portion for linking to the clearance face 130, and a substantially rectilinear portion for linking to the control face 140.

In the example illustrated in FIG. 15 as well as in FIGS. 16 to 23, the transition face 150 is purely radial, so that the angular transition length δt is zero, and the transition distance Rt varies between Rd and Rp.

The function of transition face 150 is that of linking the clearance face 130 and the control face 140. For this reason, the value of the transition distance Rt has no particular significance. It is only important that the penetration control distance Rp remain smaller than this transition distance Rt, and satisfy the relation: Rc<Rp<Rt. Said otherwise, the absolute difference Δp between the cutting distance Rc and the penetration control distance Rp remains smaller than the absolute difference Δt between the cutting distance Rc and the transition distance Rt, satisfying the relation:

$$0<\Delta p<\Delta t, \text{ with } \Delta p=|Rc-Rp| \text{ and } \Delta t=|Rc-Rt|.$$

Still referring to FIGS. 14 and 15, it appears that each flute 116 is delimited by at least two flat walls 1162, 1164. Depending on the radial thickness of the active part 118 of cutting tool 110, each flute 116 may either be open toward the outside, as represented in the figures, or closed by a bottom linking the two walls 1162 and 1164. FIGS. 20 and 21 also illustrate the range of volumes of flutes 116. FIG. 20 shows the minimum value of the volume of flutes 116. Since the angle of attack β is substantially zero in this example, wall 1162 is substantially perpendicular to the cutting envelope 122. The other wall 1164 of the flutes 116 is not perpendicular to the cutting envelope 122, so that there always remains a minimum volume of the flutes 116 at which the two walls 1162 and 1164 link up. FIG. 21 in turn shows the maximum value of volume of the flutes 116.

A cutting tool 110 corresponding to the second variant of realisation that has just been described while referring to FIGS. 14 to 23 can be applied in the field of jewelery in a method of machining a setting claw. Such a cutting tool 110 is preferably made of carbon steel or of martensitic stainless steel.

In a way common to the two variants of realisation that have just been described while referring to FIGS. 1 to 13 and 14 to 23, respectively, the active part 18, 118 of the cutting tool 10, 110 comprises in succession: a radial cutting edge 20, 120 at a cutting distance Rc from the longitudinal axis 14, 114 of the cutting tool 10, 110, a clearance face 30, 130 at a distance from the longitudinal axis 14, 114 that varies between the cutting distance Rc and a final clearance distance Rd, and a control face 40, 140 at a penetration control distance Rp from the longitudinal axis 14, 114, these distances Rc, Rd, Rp satisfying the following relation: 0 <|Rc−Rp|<|Rc−Rd|.

Moreover, the active part 18, 118 of the cutting tool 10, 110 additionally comprises a transition face 50, 150 that is at a variable distance Rt from the longitudinal axis 14, 114. This distance Rt is variable and comprised between Rp and Rd. It satisfies the relation: 0 <|Rc−Rp|<|Rc−Rt|.

It is understood that the invention is not limited to the variants and forms of realisation that have been illustrated in the figures, and extends to alternatives in the capacity of one skilled in the art.

The cutting tools 10, 110 that have been shown as examples comprise between one and four flutes, and between one and four active parts. The invention also refers to cutting tools 10, 110 having flutes and active parts numbering more than four.

The cutting tools 10, 110 that have been shown as examples comprise straight flutes and straight active parts. One could contemplate flutes and active parts that are not straight but for instance helical.

The characteristic illustrated in FIG. 10 according to which each front edge extends substantially up to the longitudinal median plane perpendicular to it, and at least one of said front edges extends beyond said longitudinal median plane perpendicular to it, can be generalised to cutting tools 84 having three flutes and three active parts, to cutting tools 86 having four flutes and four active parts, and to cutting tools having even more flutes and active parts.

In a particular variant of realisation of a cutting tool 10 as solid-type milling cutter that is illustrated in FIGS. 1 to 13, the flutes 16 exhibit two walls 162, 164 that are mutually perpendicular. This geometry of the flutes 16 is not limiting. In particular, flutes 16 could be formed by two walls 162, 164 delimiting an acute angle or an obtuse angle in transverse section. In a variant, these flutes 16 could exhibit walls 162, 164 that are non-rectilinear, and/or a rounded bottom 166.

The invention claimed is:

1. Cutting tool of a rotating type, in particular a milling cutter or borer, said cutting tool being provided with a body having a longitudinal axis and at least one flute alternating with at least one active part, wherein
each active part has a peripheral surface comprising in succession:
a radial cutting edge,
a clearance face, to favour the elimination of chips, and
a control face to control the depth of penetration of the cutting, said control face opening into a flute, and
said radial cutting edge defines a cutting envelope and is situated at a cutting distance (Rc) from said longitudinal axis,
said clearance face is defined by an angular clearance length (δd) and is situated at a distance from said longitudinal axis that is the cutting distance (Rc) at a beginning of the angular clearance length (δd) and that is a final clearance distance (Rd) at an end of the angular clearance length (δd),
said control face is defined by an angular penetration control length (δp) and is situated at a penetration control distance (Rp) from said longitudinal axis, and
the absolute difference (Δp) between said cutting distance (Rc) and said penetration control distance (Rp) is larger than zero, and smaller than the absolute difference (Δd) between said cutting distance (Rc) and said final clearance distance (Rd), satisfying the relation:

$$0<\Delta p<\Delta d, \text{ with } \Delta p=|Rc-Rp| \text{ and } \Delta d=|Rc-Rd|.$$

2. Cutting tool according to claim 1, wherein said radial cutting edge is defined by an angle of attack (β) that is substantially zero.

3. Cutting tool according to claim 1, wherein said radial cutting edge is defined by an angle of attack (β) that is negative.

4. Cutting tool according to claim 1, wherein said radial cutting edge is defined by an angle of attack (β) that is positive.

5. Cutting tool according to claim 1, wherein said clearance face is a substantially flat face.

6. Cutting tool according to claim 1, wherein said body is a cylindrical or conical or rounded-shaped body, with a radius (Rf) that coincides with the cutting distance (Rc).

7. Cutting tool according to claim 6, wherein said penetration control distance (Rp) is constant, so that said control face in a plane transverse to said longitudinal axis has a circular-arc profile.

8. Cutting tool according to claim 6, wherein said penetration control distance (Rp) is linear, so that said control face in a plane transverse to said longitudinal axis has a rectilinear profile.

9. Cutting tool according to claim 6, wherein said angular clearance length (δd) is comprised between 5° and 160°.

10. Cutting tool according to claim 6, wherein said absolute difference (Δd) between said cutting distance (Rc) and said final clearance distance (Rd) is comprised between 0.03 mm and 0.3 mm.

11. Cutting tool according to claim 6, comprising at least two flutes and at least two active parts, and wherein said angular penetration control length (δp) is comprised between 0° and 100°.

12. Cutting tool according to claim 6, comprising a single flute and a single active part, and wherein said angular penetration control length (δp) is comprised between 0° and 300°.

13. Cutting tool according to claim 6, wherein the absolute difference (Δp) between said cutting distance (Rc) and said penetration control distance (Rp) is comprised between 0.03 mm and 0.3 mm.

14. Cutting tool according to claim 6, wherein the free end of said body comprises protruding front edges, wherein each front edge extends substantially at least up to the longitudinal median plane that is perpendicular to it, and wherein at least one of said front edges extends beyond said longitudinal median plane that is perpendicular to it.

15. Cutting tool according to claim 14, wherein each of these front edges is situated in the longitudinal extension of a wall of a flute on which a radial cutting edge is resting.

16. Cutting tool according to claim 14, wherein said body comprises exactly two flutes and two active parts, and wherein said front edges are numbering two and are substantially parallel.

17. Cutting tool according to claim 14, wherein just one (92') of said front edges extends beyond said longitudinal median plane.

18. Cutting tool according to claim 1, wherein said body is an annular body with a cylindrical or conical or rounded shape, and having an inner radius (Ri) that coincides with said cutting distance (Rc).

19. Cutting tool according to claim 18, wherein said penetration control distance (Rp) is constant, so that said control face in a plane transverse to said longitudinal axis has a circular-arc profile.

20. Cutting tool according to claim 18, wherein said angular clearance length (δd) is comprised between 10° and 90°.

21. Cutting tool according to claim 18, wherein the absolute difference (Δd) between said cutting distance (Rc) and said final clearance distance (Rd) is comprised between 2% and 15% of an outer radius that is defined as the sum of the inner radius (Ri) and the thickness (Ep) of the annular body.

22. Cutting tool according to claim 18, wherein the angular penetration control length (δp) is comprised between 60° and 140°.

23. Cutting tool according to claim 18, wherein the absolute difference (Δp) between said cutting distance (Rc) and said penetration control distance (Rp) is comprised between 0.03 mm and 0.3 mm.

24. Cutting tool according to claim 1, wherein the periphery of each active part in addition comprises a transition face extending between said clearance face and said control face, said transition face being situated at a transition distance (Rt) from the longitudinal axis, and wherein the absolute difference (Δp) between the cutting distance (Rc) and the penetration control distance (Rp) is smaller than the absolute difference (Δt) between the cutting distance (Rc) and said transition distance (Rt), satisfying the relation:

$$0 < \Delta p < \Delta t, \text{ with } \Delta p = |Rc - Rp| \text{ and } \Delta t = |Rc - Rt|.$$

25. Method of preparing a root canal for an endodontic treatment, comprising applying a cutting tool according to claim 6.

26. Method of machining a setting claw in the field of jewelry, comprising applying a cutting tool according to claim 18.

* * * * *

UNITED STATES PATENT AND TRADEMARK OFFICE
CERTIFICATE OF CORRECTION

PATENT NO.       : 8,657,537 B2                                                    Page 1 of 1
APPLICATION NO. : 12/678201
DATED            : February 25, 2014
INVENTOR(S)      : Francis Delacretaz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 986 days.

Signed and Sealed this

Twenty-ninth Day of September, 2015

Michelle K. Lee
*Director of the United States Patent and Trademark Office*